United States Patent [19]

Senda et al.

[11] Patent Number: 4,808,340

[45] Date of Patent: Feb. 28, 1989

[54] PROCESS FOR PREPARING METHYL 4-OXO-5-TETRADECYNOATE

[75] Inventors: Shuji Senda; Tetsuo Omata, both of Osaka, Japan

[73] Assignee: Nitto Electric Industrial Co., Ltd., Osaka, Japan

[21] Appl. No.: 136,041

[22] Filed: Dec. 21, 1987

[30] Foreign Application Priority Data

Dec. 19, 1986 [JP] Japan .................................. 61-305030

[51] Int. Cl.$^4$ ................................................. C11C 3/04
[52] U.S. Cl. ................................ 260/410.9; 260/405.5; 558/276
[58] Field of Search ........................ 260/410.9, 405.5; 558/276

[56] References Cited

U.S. PATENT DOCUMENTS 3,801,611 4/1974 Henrick et al. ................... 260/410.9
3,801,612 4/1974 Willy et al. ....................... 260/410.9

OTHER PUBLICATIONS

Senda et al, *Chemical Abstracts*, vol. 100, No. 102990y (1984).
Baker et al, *Chemical Abstracts*, vol. 96, No. 199357g (1982).
Midland et al, *Chemical Abstracts*, vol. 95, No. 132585r (1981).
Baker et al, J. Chem. Soc., Perkin I, vol. 1982, pp. 69–71 (1982).

*Primary Examiner*—Bruce D. Gray
*Attorney, Agent, or Firm*—Sughrue, Mion, Zinn, Macpeak & Seas

[57] ABSTRACT

A process for preparing methyl 4-oxo-5-tetradecynoate useful as an intermediate for synthesizing (R,Z)-5-dec-1-enyl-oxacyclopentan-2-one, which comprises reacting monomethyl succinate with an alkyl chlorocarbonate in the presence of a base to form an acid anhydride and reacting the acid anhydride with a Grignard reagent of 1-decyne. Methyl 4-oxo-5-tetradecynoate can be prepared in high yields at high purities by this process.

9 Claims, No Drawings

PROCESS FOR PREPARING METHYL 4-OXO-5-TETRADECYNOATE

FIELD OF THE INVENTION

This invention relates to a process for preparing methyl 4-oxo-5-tetradecynoate.

BACKGROUND OF THE INVENTION

Methyl 4-oxo-5-tetradecynoate is a compound represented by formula:

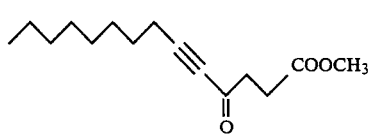

and is an important intermediate for synthesizing (R,Z)-5-dec-1-enyloxacyclopentan-2-one, which is a sex pheromone of Japanese beetles (*Popillia japonica*) having done much harm in U.S.A. and has been used as an attractant for Japanese beetles. As shown by Reaction Scheme I, (R,Z)-5-dec-1-enyloxacyclopentan-2-one (4) can be obtained by asymmetrically reducing methyl 4-oxo-5-tetradecynoate (1) to convert it to the corresponding alcohol (2), subjecting the alcohol (2) to hydrolysis and cyclization to form a lactone (3), and partially reducing the lactone (3).

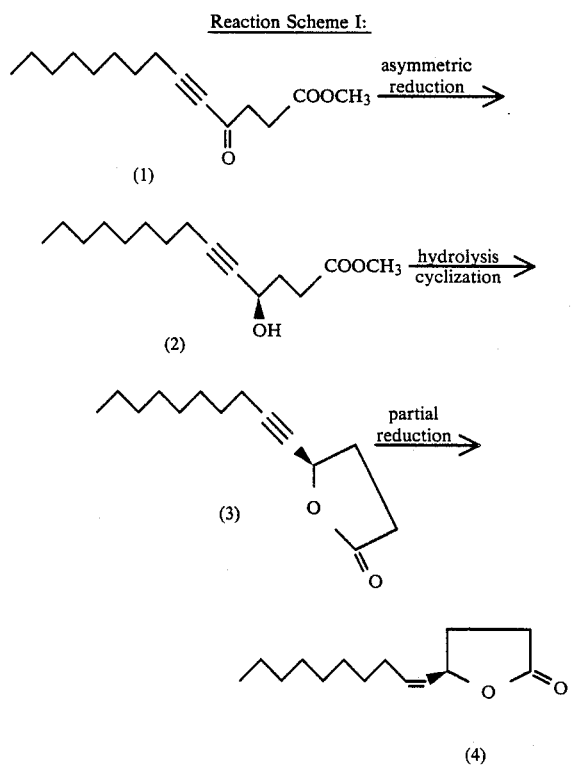

Conventionally known processes for preparing methyl 4-oxo-5-tetradecynoate include (a) the process of R. Baker et al., *J. Chem. Soc.*, Perkin I, 69 (1982), (b) the process of M. M. Midland et al., *J. Org. Cem.*, Vol. 46, 4108 (1981), and (c) the process of S. Senda et al., *Argric. Biol. Chem.*, Vol. 47, 2595 (1983) as illustrated below.

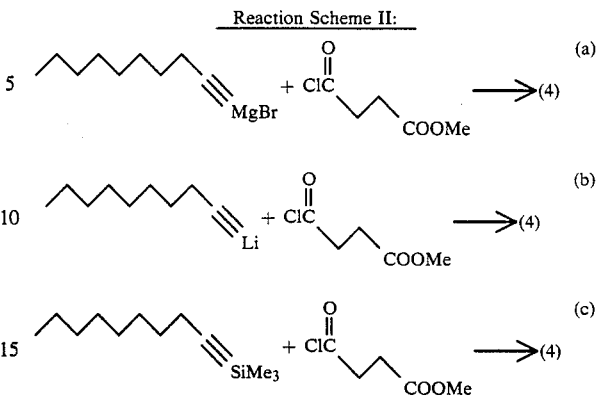

The processes (a) and (b) attain very low yields of the compound (1). The process (c), though achieving relatively high yields, encounters difficulty in separation of by-products, failing to obtain the compound (4) at high purity. Moreover, all of these conventional processes entail extremely high cost of production. More specifically, any of them uses an expensive acid chloride. In particular, the process (b) needs expensive lithium compounds, e.g., n-butyl lithium, and the process (c) also requires lithium compounds and chlorotrimethylsilane.

SUMMARY OF THE INVENTION

Accordingly, one object of this invention is to provide a novel process for preparing methyl 4-oxo-5-tetradecynoate in high yield and at high purity.

Another object of this invention is to provide a novel process for preparing methyl 4-oxo-5-tetradecynoate starting with an inexpensive compound.

The inventors have conducted extensive investigations to solve the above-described problems associated with the preparation of methyl 4-oxo-5-tetradecynoate. As a result, it has now been found that the desired compound can be obtained easily in high yield and at high purity by reacting inexpensive monomethyl succinate with an alkyl chlorocarbonate in the presence of a base and reacting the resulting acid anhydride with a Grignard reagent of 1-decyne.

The present invention relates to a process for preparing methyl 4-oxo-5-tetradecynoate, which comprises reacting monomethyl succinate with an alkyl chlorocarbonate in the presence of a base to form an acid anhydride and reacting the resulting acid anhydride with a Grignard reagent of 1-decyne.

DETAILED DESCRIPTION OF THE INVENTION

The process according to the present invention is illustrated by the following reaction scheme:

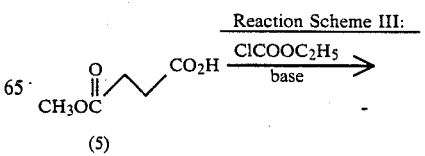

-continued
Reaction Scheme III:

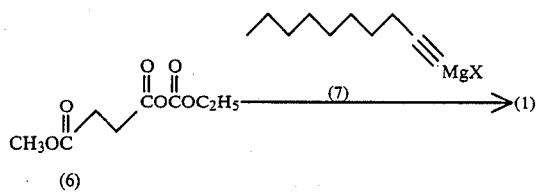

wherein X represents a halogen atom.

The reaction between monomethyl succinate (5) and an alkyl chlorocarbonate is carried out in an organic solvent in the presence of a base. The alkyl chlorocarbonate which can be used in this reaction is not particularly limited and usually includes an ethyl ester to advantage. The base to be used is not also particularly limited as long as it is capable of scavenging hydrogen chloride produced by the reaction and does not hinder the reaction. Such a base preferably includes organic bases, e.g., alkylamines (e.g., trimethylamine, triethylamine, etc.), pyridine, etc.

The organic solvent to be used preferably but unrestrictedly include hydrocarbons, e.g., benzene, toluene, hexane, and ethers, e.g., diethyl ether, tetrahydrofuran. The reaction temperature is usually room temperature or lower, and preferably 0° C. or lower.

The acid anhydride (6) is then reacted with a Grignard reagent of 1-decyne. The reaction may be effected by adding a Grignard reagent of 1-decyne dropwise to the reaction mixture containing the acid anhydride (6) as produced, or the latter may be added dropwise to the former. This reaction is usually carried out at room temperature or a lower temperature, and preferably at 0° C. or lower.

The Grignard reagent of 1-decyne is used in an amount of from 0.5 to 1.5 equivalent, and preferably from 0.8 to 1.0 equivalent, based on the monomethyl succinate.

The Grigard reagent of 1-decyne can easily be prepared in a usual manner by, for example, reacting an alkyl- or arylmagnesium halide, e.g., methylmagnesium iodide, ethylmagnesium bromide, a chlorophenylmagnesium halide, etc., with decyne in a solvent, such as ethers, e.g., diethyl ether, tetrahydrofuran, etc.

After the reaction, water is added to the reaction mixture, and the organic layer separated is concentrated and subjected to distillation to obtain methyl 4-oxo-5-tetradecynoate in a high yield at a high purity.

As described above, starting with inexpensive monomethyl succinate, the process of the present invention produces methyl 4-oxo-5-tetradecynoate in high yields at high purities.

The present invention is now illustrated in greater detail with reference to Example, but it should be understood that the present invention is not deemed to be limited thereto.

EXAMPLE 1

In 3 l of toluene was dissolved 317 g of monomethyl succinate, and 350 ml of triethylamine was added to the solution. Ethyl chlorocarbonate was added dropwise to the solution while maintaining at a temperature between −20° C. and −30° C., followed by stirring for 2 hours to obtain a reaction mixture containing an acid anhydride.

Separately, 54 g of magnesium and 180 ml of ethyl bromide were reacted in 1.5 l of tetrahydrofuran to prepare ethylmagnesium bromide. In 100 ml of tetrahydrofuran was dissolved 360 ml of decyne, and the resulting solution was added dropwise to the above-obtained Grignard reagent solution at room temperature, followed by stirring for 3 hours to obtain a Grignard reagent of decyne.

The above-obtained acid anhydride solution was cooled to −40° C., and the Grignard reagent of decyne was added thereto dropwise at that temperature. After the addition, the mixture was stirred for 1.5 horus. Water was added to the reaction mixture, and the organic layer separated was dried, concentrated, and distilled to obtain 430 g (yield: 94% based on the decyne) of methyl 4-oxo-5-tetradecynoate having a boiling point of from 146° to 150° C./0.5 mmHg. The purity of the product was found to be 98.5% as determined by gas chromatography (5% FFAP column, 3 mm (D)×2 m (H); carrier gas: 1.0 Kg/cm$^2$ of N$_2$; retension time: 10.46 min).

While the invention has been described in detail and with reference to specific embodiments thereof, it will be apparent to one skilled in the art that various changes and modifications can be made therein without departing from the spirit and scope thereof.

What is claimed is:

1. A process for preparing methyl 4-oxo-5-tetradecynoate, which comprises reacting monomethyl succinate with an alkyl chlorocarbonate in the presence of a base to form an acid anhydride and reacting the acid anhydride with a Grignard reagent of 1-decyne.

2. A process as claimed in claim 1, wherein said alkyl chlorocarbonate is ethyl chlorocarbonate.

3. A process as claimed in claim 1, wherein said base is an organic base.

4. A process as claimed in claim 1, wherein said reacting between monomethyl succinate and the alkyl chlorocarbonate is at room temperature or a lower temperature.

5. A process as claimed in claim 1, wherein said reacting between monomethyl succinate and the alkyl chlorocarbonate is at 0° C. or a lower temperature.

6. A process as claimed in claim 1, wherein said reacting between the acid anhydride and the Grignard reagent of 1-decyne is at room temperature or a lower temperature.

7. A process as claimed in claim 1, wherein said reacting between the acid anhydride and the Grignard reagent of 1-decyne is at 0° C. or a lower temperature.

8. A process as claimed in claim 1, wherein said Grignard reagent of 1-decyne is used in an amount of from 0.5 to 1.5 equivalent based on the monomethyl succinate.

9. A process as claimed in claim 1, wherein said Grignard reagent of 1-decyne is used in an amount of from 0.8 to 1.0 equivalent based on the monomethyl succinate.

* * * * *